(12) United States Patent
Ruan et al.

(10) Patent No.: US 7,931,811 B2
(45) Date of Patent: Apr. 26, 2011

(54) DIELECTRIC BARRIER REACTOR HAVING CONCENTRATED ELECTRIC FIELD

(75) Inventors: Rongsheng Ruan, Arden Hills, MN (US); Shaobo Deng, St. Paul, MN (US); Ling Chen, St. Paul, MN (US); Xingyang Lin, St. Paul, MN (US); Lloyd Metzger, Brookings, SD (US)

(73) Assignee: Regents of The University of Minnesota, Minneapolis, MN (US)

( * ) Notice: Subject to any disclaimer, the term of this patent is extended or adjusted under 35 U.S.C. 154(b) by 1185 days.

(21) Appl. No.: 11/588,955

(22) Filed: Oct. 27, 2006

(65) Prior Publication Data

US 2008/0099406 A1    May 1, 2008

(51) Int. Cl.
C02F 1/48    (2006.01)

(52) U.S. Cl. .................. 210/748.01; 422/22; 422/186

(58) Field of Classification Search .......... 210/748.01; 422/22
See application file for complete search history.

(56) References Cited

U.S. PATENT DOCUMENTS

| | | |
|---|---|---|
| 2,345,798 A | 4/1944 | Daily |
| 3,865,733 A | 2/1975 | Taylor .......................... 250/532 |
| 3,898,468 A | 8/1975 | Guerin ......................... 250/535 |
| 3,970,905 A | 7/1976 | Iyoh et al. ................. 317/262 E |
| 4,085,170 A | 4/1978 | Simpson et al. ................... 261/1 |
| 4,244,712 A | 1/1981 | Tongret ........................ 55/124 |
| 4,391,773 A | 7/1983 | Flanagan ....................... 422/22 |
| 4,863,701 A | 9/1989 | McMurray ............... 422/186.08 |
| 5,304,486 A | 4/1994 | Chang ........................... 435/287 |
| 5,326,530 A | 7/1994 | Bridges ......................... 422/22 |
| 5,370,846 A | 12/1994 | Yokomi et al. ........... 422/186.07 |
| 5,411,713 A | 5/1995 | Iwanaga .................... 422/186.15 |
| 5,427,747 A | 6/1995 | Kong et al. .................... 422/186 |
| 5,458,748 A | 10/1995 | Breault et al. ................. 204/177 |
| 5,516,493 A | 5/1996 | Bell et al. ................. 422/186.07 |
| 5,549,874 A | 8/1996 | Kamiya et al. ........... 422/186.04 |
| 5,603,893 A | 2/1997 | Gundersen et al. ............. 422/22 |
| 5,637,198 A | 6/1997 | Breault ........................ 204/165 |
| 5,670,122 A | 9/1997 | Zamansky et al. ............. 423/210 |
| 5,681,533 A | 10/1997 | Hiromi ......................... 422/121 |
| 5,695,619 A | 12/1997 | Williamson et al. ........... 204/165 |
| 5,711,147 A | 1/1998 | Vogtlin et al. ................... 60/274 |
| 5,746,984 A | 5/1998 | Hoard ........................... 422/169 |
| 5,750,823 A | 5/1998 | Wofford et al. ............... 588/210 |

(Continued)

FOREIGN PATENT DOCUMENTS

DE         43 32 866 A1    3/1995

(Continued)

OTHER PUBLICATIONS

Database WPI, Section Ch, Week 200123, KR 2000053 747 A( Human Mediteck Co Ltd), (report XP-002327531), Derwent Publications Ltd., London, G.B., Class D22 AN 2001-223586, Sep. 5, 2000. (Abstract).

(Continued)

*Primary Examiner* — Walter D Griffin
*Assistant Examiner* — Cameron J Allen
(74) *Attorney, Agent, or Firm* — David D. Brush; Westman, Champlin & Kelly, P.A.

(57) ABSTRACT

A fluid treatment device and method are provided for generating an electric field across a gap between first and second electrode and for concentrating the electric field within a fluid treatment chamber located in the gap.

18 Claims, 7 Drawing Sheets

U.S. PATENT DOCUMENTS

| | | | |
|---|---|---|---|
| 5,759,497 A | 6/1998 | Kuzumoto et al. | 422/186.07 |
| 5,822,981 A | 10/1998 | Williamson et al. | 60/275 |
| 5,836,154 A | 11/1998 | Williamson et al. | 60/275 |
| 5,843,288 A | 12/1998 | Yamamoto | 204/164 |
| 5,843,383 A | 12/1998 | Williamson et al. | 422/186.04 |
| 5,855,855 A | 1/1999 | Williamson et al. | 422/186.04 |
| 5,871,703 A | 2/1999 | Alix et al. | 423/210 |
| 5,891,409 A | 4/1999 | Hsiao et al. | 423/239.1 |
| 5,893,267 A | 4/1999 | Vogtlin et al. | 60/274 |
| 5,895,558 A | 4/1999 | Spence | 204/164 |
| 5,895,632 A | 4/1999 | Nomura et al. | 422/186.04 |
| 5,904,905 A | 5/1999 | Dolezal et al. | 422/186.04 |
| 6,030,506 A | 2/2000 | Bittenson et al. | 204/164 |
| 6,096,564 A | 8/2000 | Denes et al. | 438/1 |
| 6,146,599 A | 11/2000 | Ruan et al. | 422/186.04 |
| 6,171,450 B1 | 1/2001 | Behnisch et al. | 204/164 |
| 6,176,078 B1 | 1/2001 | Balko et al. | 60/275 |
| 6,228,330 B1 | 5/2001 | Herrmann et al. | 422/186.05 |
| 6,451,252 B1 | 9/2002 | Ruan et al. | 422/22 |
| 6,455,014 B1 | 9/2002 | Hammerstrom et al. | 422/186.04 |
| 6,558,638 B2 | 5/2003 | Zakiraka et al. | 422/186.04 |
| 6,562,386 B2 | 5/2003 | Ruan et al. | 426/237 |
| 6,818,193 B2 | 11/2004 | Christodoulatos et al. | 423/210 |
| 2003/0132100 A1 | 7/2003 | Crowe et al. | 204/164 |
| 2003/0146310 A1* | 8/2003 | Jackson | 239/690 |
| 2003/0180421 A1 | 9/2003 | Ruan et al. | 426/237 |

FOREIGN PATENT DOCUMENTS

| | | |
|---|---|---|
| DE | 196 35 231 A1 | 3/1998 |
| DE | 19717169 A1 | 10/1998 |
| EP | 0 287 480 | 10/1988 |
| FR | 2 759 590 | 8/1998 |
| GB | 2316017 | 2/1998 |
| JP | 59-069404 | 4/1984 |
| JP | 2-211218 | 8/1990 |
| JP | 2-211219 | 8/1990 |
| JP | 4-122417 | 4/1992 |
| JP | 4-247218 | 9/1992 |
| JP | 07 256056 | 10/1995 |
| JP | 10-118448 | 5/1998 |
| JP | 10-235138 | 9/1998 |
| JP | 2000093967 | 4/2000 |
| SU | 1271554 A1 | 11/1986 |
| SU | 1495286 A | 7/1989 |
| WO | WO 95/09256 | 4/1995 |
| WO | WO 98/00342 | 1/1998 |
| WO | WO 99/46201 | 9/1999 |
| WO | WO 01/52910 | 7/2001 |

OTHER PUBLICATIONS

Kimberly Kelly Wintenberg et al., Air Filter Sterilization Using a One Atmosphere Uniform Glow Discharge Plasma (the Volfilter), IEEE Transactions on Plasma Science, Feb. 2000, vol. 28, No. 1. (Abstract).

Thomas C. Montie et al., An Overview of Research Using the One Atmosphere Uniform Glow Discharge Plasma for Sterilization of Surfaces and Materials, IEEE Transactions on Plasma Science, Feb. 2000, vol. 28, No. 1. (Abstract).

J. Reece Roth et al., A Remote Exposure Reactor (RER) for Plasma Processing and Sterilization by Plasma Active Species at One Atmosphere, IEEE Transactions on Plasma Science, Feb. 2000, vol. 28., No. 1. (Abstract).

Joseph G. Birmingham et al., Bacterial Decontamination Using Ambient Pressure Nonthermal Discharge, IEEE Transactions on Plasma Science, Feb. 2000, vol. 28, No. 1. (Abstract).

K. Kelly-Wintenberg et al., Use of a One Atmosphere Uniform Glow Discharge Plasma to Kill a Broad Spectrum of Microorganisms, J. Vac. Sci. Technol., Jul./Aug. 1999. (Abstract).

* cited by examiner

DIELECTRIC BARRIER REACTOR HAVING CONCENTRATED ELECTRIC FIELD

CROSS-REFERENCE TO RELATED APPLICATION

None.

FIELD OF THE DISCLOSURE

The present disclosure relates to dielectric barrier reactors for treating liquids and other fluids to destroy live pathogens living in the fluid or for decomposing hazardous compounds contained in the fluid.

BACKGROUND OF THE DISCLOSURE

A variety of methods and apparatus have been used in an effort to kill live pathogens or decompose hazardous compounds within a fluid. One common approach for treating a liquid, known as a pulsed electric field (PEF) process, applies a high frequency pulsed DC voltage to two metal electrodes, which form a treatment chamber between them. The liquid to be treated is passed through the treatment chamber and is in direct physical and electrical contact with the electrodes. The high frequency pulse is intended to prevent electric current from following through the liquid, which can cause unwanted heating.

One disadvantage of the PEF process is that good bacteria kills are often accompanied by a corresponding temperature rise in the liquid being treated This heat can easily damage active components, ingredients or other desirable characteristics of the liquid, such as food nutrients and sensory attributes, including flavors, aromas and colors. If these products are processed they can become unacceptable or their commercial value can be greatly reduced. In the case of biological fluids, living cells may be altered or damaged.

Another disadvantage of the PEF process is the high costs associated with special power supplies that are required to produce the high frequency pulsed DC voltage. Further, the electrodes tend to corrode due to the direct contact between the electrodes and the liquid being treated. Also, since the electrodes are immersed directly in the liquid, the electrodes can be regarded as a major contamination source to the liquid due to oxidation of the electrodes during discharge. The electrodes must therefore be replaced regularly, which further increases maintenance time and costs.

Improved methods and apparatus are desired for treating fluids without decreasing the natural characteristics of the fluid.

SUMMARY

An embodiment of the disclosure is directed to a fluid treatment device, which includes first and second electrodes arranged to generate an electric field across a gap between the electrodes. A fluid treatment chamber is located within the gap and is electrically isolated from the first and second electrodes. An electric field concentrator concentrates the electric field within the fluid treatment chamber.

Another embodiment of the disclosure is directed to a method, which includes: generating an electric field across a gap between first and second electrodes; positioning a liquid within a fluid treatment chamber located within the gap; and concentrating the electric field within the fluid treatment chamber to treat the liquid.

DETAILED DESCRIPTION OF ILLUSTRATIVE EMBODIMENTS

In one embodiment of the present disclosure, a fluid treatment device is used to destroy live pathogens or breakdown hazardous compounds in a fluid by concentrating an electric field produced by the device within the fluid being treated.

Figure 1:
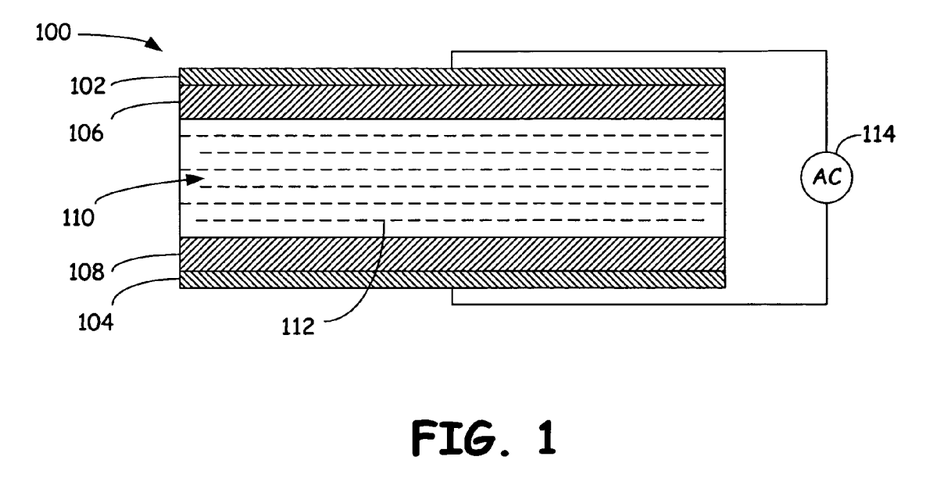
FIG. 1 is a diagram, which schematically illustrates the basic components of a fluid treatment device according to an embodiment of the present invention.

FIG. 1 is a diagram, which schematically illustrates basic components of a fluid treatment device according to an embodiment of the present invention. Device 100 includes electrodes 102 and 104, dielectric barriers 106 and 108 and a gap 110 between the barriers. The various layers within device 300 can be separated by suitable spacers or side walls (not shown), for example. Gap 110 can be referred to as a reaction volume or treatment chamber. A fluid 112 being treated is placed in gap 110 or passed through gap 110 from an inlet to an outlet of the device. In one embodiment, fluid 112 includes a liquid. Each of the electrodes 102 and 104 is physically an electrically isolated from the liquid in gap 110 by a respective one of the dielectric barriers 102 and 104.

Device 100 uses a low cost, low frequency alternating current (AC) power supply 114, which applies an AC voltage to the pair of electrodes 102 and 104. Alternatively, power supply 114 can include a pulsed DC power supply, for example. Other types of power supplies can also be used, and their output voltages can have any suitable waveform, such as sinusoidal, square, or triangular.

During operation, the AC voltage applied to electrodes 102 and 104 generates an electric field across gap 110. Dielectric barriers 106 and 108 prevent current from flowing through the liquid 112 in gap 110. Barriers 106 and 108 also physically isolate the liquid 112 from the electrodes 102 and 104 to help prevent corrosion of the electrodes and contamination of the liquid.

Figure 2:
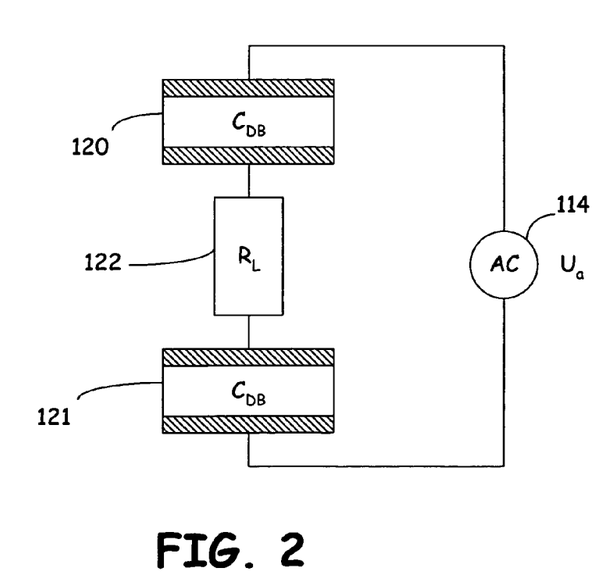
FIG. 2 illustrates an analogous circuit for the fluid treatment device shown in FIG. 1.

FIG. 2 illustrates an analogous circuit for the fluid treatment device 100 shown in FIG. 1, where individual components of the device are treated as capacitors or resistors. Dielectric barriers 106 and 108 are represented as capacitors 120 and 121, each of which having a capacitance $C_{DB}$. Liquid 112 is represented as a resistor 122, which has a resistance $R_L$. Power supply 114 applies a voltage $U_a$, which is distributed the dielectric barrier layers and the liquid layer. The inventors of the present application have determined that the ideal situation is to have all of the voltage distributed to the liquid layer. As discussed in more detail below, one or more embodiments of the present disclosure ensure a large distribution of voltage to the liquid layer.

When analyzing the voltage distribution in the circuit shown in FIG. 2, the electric current in the series circuit is:

$$I = \frac{U_a}{Z} \quad \text{Eq. 1}$$

where $U_a$ is the total supplied voltage and Z is the total impedance, which is:

$$Z = 2Z_{DB} + Z_L = \frac{2}{2\pi f C_{DB}} + R_L \quad \text{Eq. 2}$$

where $Z_{DB}$ and $Z_L$ are the impedances for the dielectric barriers and liquid being treated, respectively, and $Z_L = R_L$, the resistance of the liquid. $C_{DB}$ is the capacitance for the dielectric barrier, and f is the frequency of the applied voltage.

Substituting Equation 2 into Equation 1 provides:

$$I = \frac{\pi f C_{DB}}{1 + \pi f C_{DB} R_L} U_a \quad \text{Eq. 3}$$

Therefore, the voltage applied to the liquid is defined as:

$$U_L = IR_L = \frac{\pi f C_{DB}}{1 + \pi f C_{DB} R_L} U_a \times R_L \quad \text{Eq. 4}$$

where $$C_{DB} = \frac{\varepsilon_0 \varepsilon_r A_{DB}}{d_{DB}} \quad \text{Eq. 5}$$

and $$R_L = \frac{d_L}{\sigma \cdot A_L} \quad \text{Eq. 6}$$

Equation 5 shows that the capacitance (C) is a function of the absolute dielectric constant ($\varepsilon_0$) and relative dielectric constant ($\varepsilon_r$) of the dielectric barrier material, area ($A_{DB}$) of the planes formed by the dielectric barriers, and the distance ($d_{DB}$) between the two planes of the capacitor.

Equation 6 indicates that the resistance of the liquid ($R_L$) is a function of the electrical conductivity ($\sigma$) of the liquid, the length of the resistor (thickness of the liquid layer) ($d_L$), and the area of the liquid layer ($A_L$).

The electric field ($E_L$) across a liquid layer having a thickness of $d_L$ can be described as:

$$E_L = \frac{U_L}{d_L} \quad \text{Eq. 7}$$

Substituting Equations 4, 5 and 6 into Equation 7 produces the relation:

$$E_L = \frac{\pi f \varepsilon_0 \varepsilon_r A_{DB}}{\sigma \cdot d_{DB} A_L + \pi f \varepsilon_0 \varepsilon_r A_{DB} d_L} \times U_a \quad \text{Eq. 8}$$

Rearranging Equation 8 results in:

$$E_L = \frac{\pi f \varepsilon_0}{\frac{\sigma \cdot d_{DB} A_L}{\varepsilon_r A_{DB}} + \pi f \varepsilon_0 d_L} \times U_a \quad \text{Eq. 9}$$

Equation 9 indicates that if $$\frac{\sigma \cdot d_{DB} A_L}{\varepsilon_r A_{DB}}$$

is negligible, i.e., $$E_L \propto \frac{U_a}{d_L},$$

most of the applied voltage would be directed to the liquid being treated. In other words, if a very thin (small $d_{DB}$) dielectric material having a very high dielectric constant (high $\varepsilon_r$) is used or if the ratio $A_L$ to $A_{DB}$ is very small, a very high electric field can be generated across the liquid. Since it can be impractical to find a material with a very high dielectric constant with a very high voltage breakdown strength, it may be more practical to change the area ratio in order to concentrate the electric field within the liquid.

Figure 3:
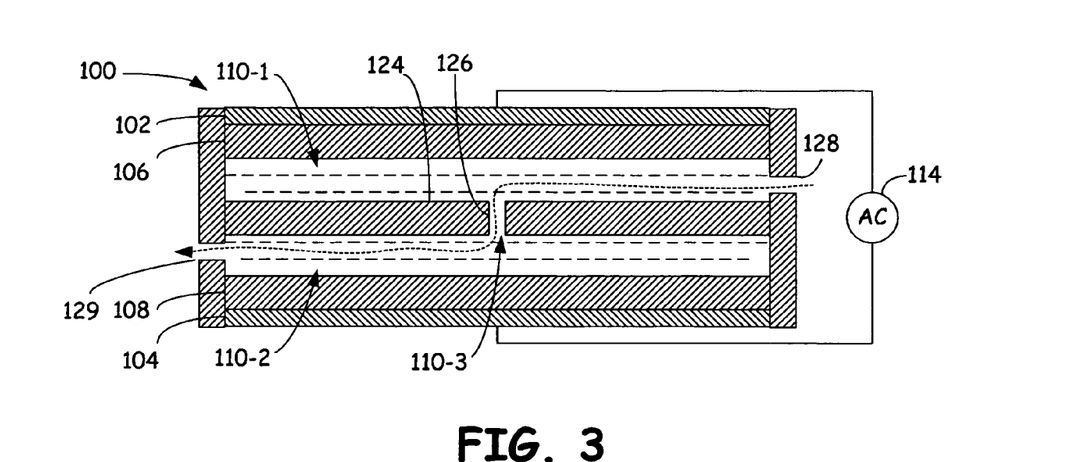
FIG. 3 is a diagram, which illustrates the fluid treatment device as modified to further include a dielectric separator.

FIG. 3 is a diagram, which illustrates fluid treatment device 100 as modified to further include a dielectric separator 124, which separates gap 110 into two bulk liquid (BL) treatment chambers 110-1 and 110-2. Separator 124 has narrow liquid channel (LC) or aperture 126, which forms a small liquid treatment chamber 110-3 between bulk liquid treatment chambers 110-1 and 110-2. If the relative dielectric constant of the separator material is larger than that of the liquid being treated, then liquid channel 110-3 also forms an electric field passageway through the dielectric separator.

In one embodiment, device 100 is configured to pass the liquid being treated along a flow path through the device, such as from an inlet 128 into liquid treatment chamber 110-1, through liquid channel 110-3, into liquid treatment chamber 110-2 to outlet 129. Other flow paths and configurations can also be used in alternative embodiments.

Figure 4:
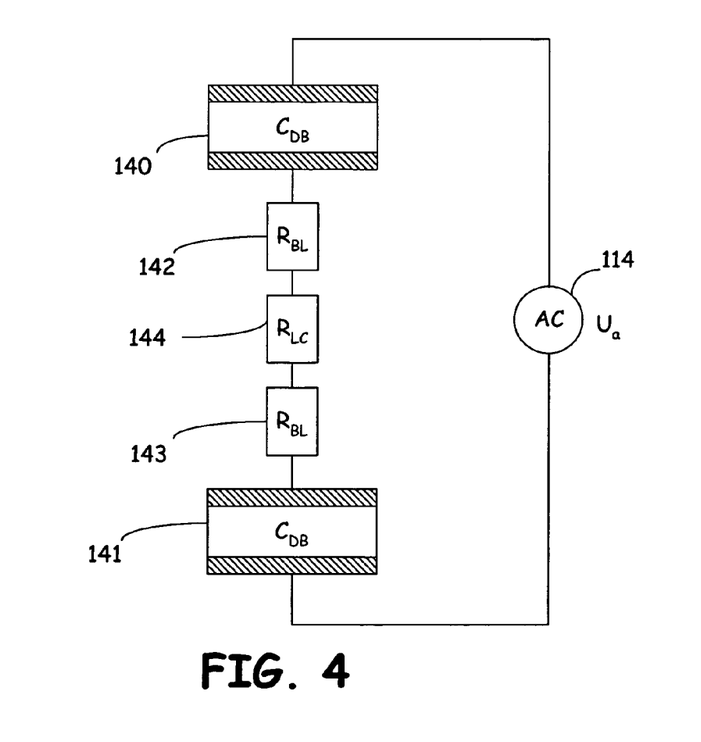
FIG. 4 is a diagram illustrating an analogous circuit for fluid treatment device shown in FIG. 3.

FIG. 4 is a diagram illustrating an analogous circuit for fluid treatment device 100 shown in FIG. 3, where the individual components of the device are treated as capacitors or resistors. Capacitors 140 and 141 represent the capacitance $C_{DB}$ of the dielectric barriers 102 and 104, respectively, resistors 142 and 143 represent the resistances $R_{BL}$ of the bulk liquid treatment chambers 110-1 and 110-2, respectively, and resistor 144 represents the resistance $R_{LC}$ of the liquid channel 110-3.

The total resistance of the liquid in the liquid treatment chamber, which includes the bulk liquid (BL) treatment chambers 110-1 and 110-2 and the liquid channel (LC) 110-3, is the sum of the three resistances:

$$R_L = 2R_{BL} + R_{LC} \quad \text{Eq. 10}$$

Since the area $A_{BL} = A_{DB}$ is one or more orders of magnitude larger than the area $A_{LC}$, the value of $R_{BL}$ can be omitted for convenience. Therefore with $R_L = R_{LC}$, we have:

$$E_{LC} = \frac{\pi f \varepsilon_0}{\frac{\sigma \cdot d_{DB} A_{LC}}{\varepsilon_r A_{DB}} + \pi f \varepsilon_0 d_{LC}} \times U_a \quad \text{Eq. 11}$$

Equation 11 indicates that the new configuration allows the ratio $A_{LC}/A_{DB}$ to be manipulated so that the electrical field across $R_{LC}$ is very high.

Figure 5:
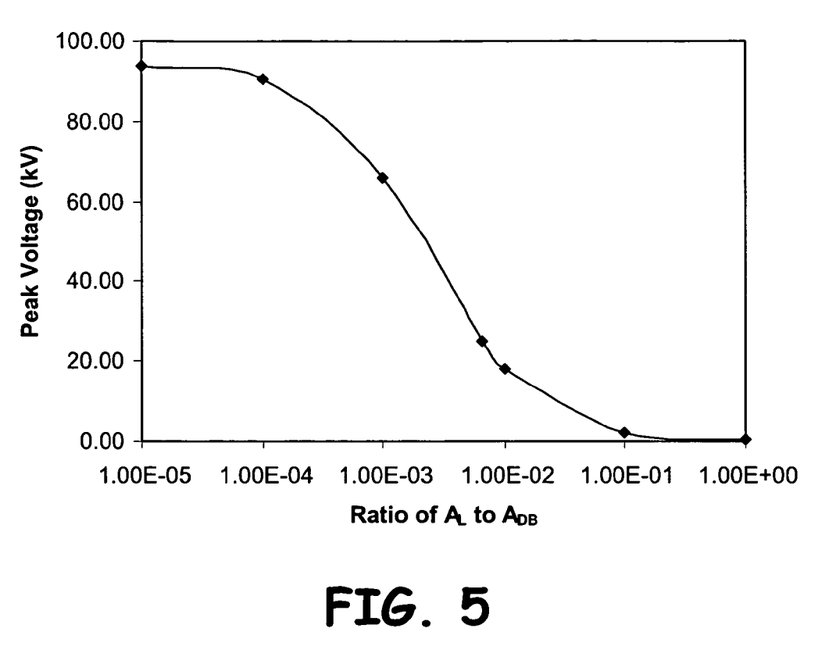
FIGS. 5 and 6 are graphs showing an effect of changing an area ratio on peak voltage when the treated liquid includes water and milk, respectively.
Figure 6:
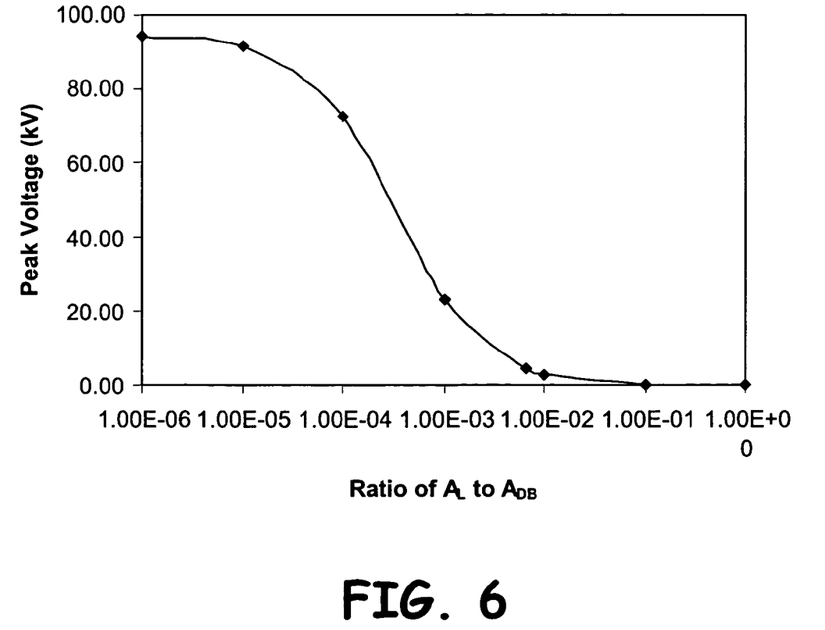

FIGS. 5 and 6 show the effect of changing the area ratio on the peak voltage ($U_a\sqrt{2}$) when the treated liquid includes water and milk, respectively. In each figure, the ratio $A_L$ to $A_{DB}$ is plotted along the horizontal axis, and the peak voltage (kV/cm) is plotted along the vertical axis.

Specifically, FIGS. 5 and 6 plot the peak voltage of the electric field $E_{LC}$ across liquid channel 110-3 according to Equation 11 for various ratios of $A_L$ to $A_{DB}$, wherein f=600 Hz, $U_a$=20 kV, $d_{DB}$=0.38 mm, $\varepsilon_{rdb}$=12.5, and $d_{LC}$=3 mm and the peak voltage is the RMS voltage drop across $d_{LC}$ times the square root of two. The calculated data shows that ratios of $A_{LC}/A_{DB}$ of $1\times10^{-4}$ and $1\times10^{-5}$ are sufficient to achieve an electric field strength of at least 25 kV/cm in both water and milk, which is sufficient to inactivate bacteria contained in the liquid. Other parameters can be used in alternative embodiments.

Referring back to FIG. 3, separator 124 therefore acts an electric field concentrator which concentrates the electric field within a portion of the liquid treatment chamber 110 that corresponds to the small liquid channel 110-3.

Figure 7:
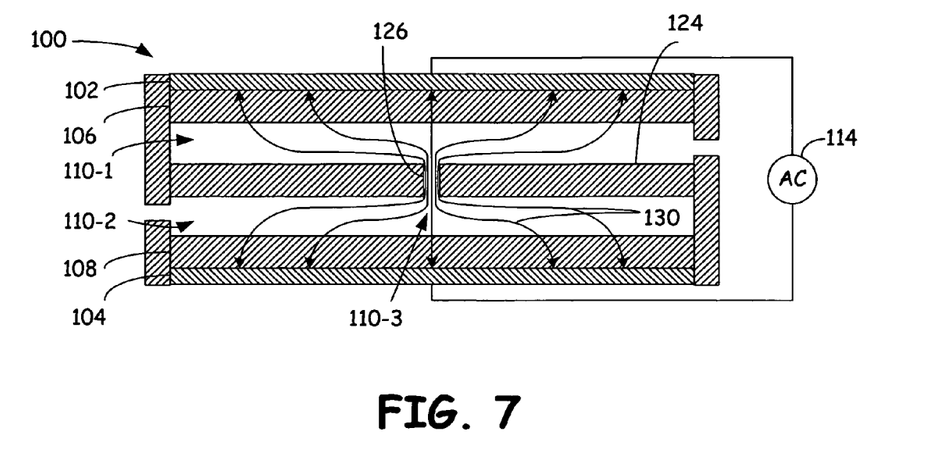
FIG. 7 is a simplified, schematic cross-sectional view of the device shown in FIG. 3, which illustrates concentration of electric field lines of force between electrodes in the device.

FIG. 7 is a simplified, schematic cross-sectional view of device 100, which illustrates the concentration of electric field lines of force 130 between electrodes 102 and 104. As mentioned above, dielectric separator 124 is electrically non-conducting and has one or more apertures 126 that form a small liquid channel 110-3 through the separator. The electric field lines of force 130 are concentrated within liquid channel 110-3 relative to the concentration within bulk liquid chambers 110-1 and 110-2.

Power supply 114 can have any suitable frequency and voltage output for achieving the desired effects. These values can be a function of desired electric field across $E_{LC}$ across the liquid channel and any desired values for the various other parameters in Equation 11. For example, power supply 114 can be configured to supply an output having a voltage in the range of 110V to 100 kV and a frequency of 50 Hz to 50 kHz, but can also be configured to supply an output outside these ranges. In one embodiment, power supply 114 is configured to supply a standard utility line voltage of 110V at 60 Hz.

Higher frequencies can be used help to concentrate the electric field within the small liquid channel, but higher frequencies can also create more heat. However, the liquid flow rate through the treatment chamber can be increased to reduce temperature effects. Also, the device can be modified to include other features that can provide for sufficient cooling, as described in more detail below.

According to Equation 11, a lower applied voltage can be used while still achieving a sufficient electric field $E_{LC}$ if a thinner dielectric barrier is used that has a sufficiently high relative dielectric constant and if the ratio $A_{LC}/A_{DB}$ is sufficiently small. If a higher applied voltage $U_a$ is used, a thicker dielectric barrier and a higher ratio $A_{LC}/A_{DB}$ can be used. The applied voltage of $U_a$ and frequency f can therefore be adjusted with the other variables in Equation 11 to achieve a desired electric field for a particular application and for a particular configuration of the device and its component parts, such as the dimensions of the structure, the aperture size and thickness and the conductivity of the liquid being treated, for example.

Electrodes 102 and 104 can have a variety of configurations in alternative embodiments. For example, electrodes 102 and 104 can be formed of thin planar sheets of conductive metal such as a copper foil or of a semiconductor. Other conductive or semi-conductive structures can also be used such as a mesh, wire or strip. The combination of electrodes 102 and 104 can have a variety of different types, such as plate-to-plate, mesh-to-mesh, plate-to-wire, wire-to-wire, plate-to-mesh, and wire-to-mesh, for example. The plates can be planar or cylindrical, for example. Electrodes 102 and 104 can be arranged coaxially with one another, wherein the outer electrode is tubular and the inner electrode is either tubular or a wire. The separator 124 would simply be positioned between the two electrodes and would have a suitable shape. Other arrangements can also be used.

In each arrangement, electrodes 102 and 104 may be physically and electrically isolated from the liquid chamber by dielectric barriers 106 and 108 in order to prevent an electrical conduction path through the liquid and contamination of liquid due to contact with the electrodes.

Dielectric barriers 106 and 108 can include any material having a suitable relative dielectric constant. In one embodiment, preferred dielectric constants range from 3-300. The higher the relative dielectric constant the better the performance. For example, dielectric barriers 106 and 108 can include plastic, Teflon® (registered trademark of E. I. du Pont de Nemours and Company), glass, ceramic, epoxy resin, and aluminum oxide. An example of a ceramic includes Strontium Titanate ($SrTiO_3$). Other electrical insulating materials can also be used. Similarly, separator 124 can be formed of any dielectric, electrically-insulating material similar to those mentioned with respect to dielectric barriers 106 and 108.

As mentioned above, separator 124 can have any number or arrangement of apertures 126, and each aperture can have any suitable shape or location. For example, aperture 126 can be circular, elliptical, rectangular, oval or a combination of shapes. An example of an oval shape includes an elongated slot defined by an entirely rounded rectangle. However, the perimeter of aperture 126 can have any curvilinear or rectilinear shape. A curvilinear shape may be preferred for avoiding electric field edge effects.

Figure 8:
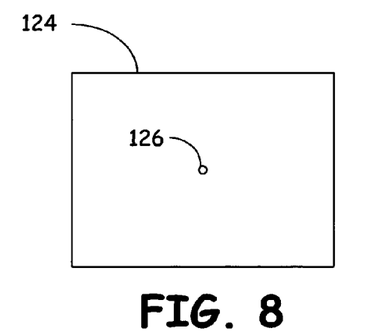
FIG. 8 illustrates a top plan view of the separator shown in FIGS. 3 and 7.

In one embodiment, separator 124 has a single, circular hole located at the geometric center of the separator, as shown in FIG. 8. FIG. 8 illustrates a top plan view of separator 124. In this example, aperture 126 has perimeter with a circular cross-sectional shape in a dimension that is parallel to the faces of electrodes 102 and 102 (shown in FIGS. 3 and 7).

Further, in some embodiments it may be preferred that aperture 126 is completely surrounded by material of separator 124 to further avoid edge effects. In these embodiments, aperture 126 has a perimeter defined entirely by sidewalls that are formed by material of separator 124. In these embodiments, aperture 126 would not be located along an edge of separator 124.

As shown in FIG. 8, aperture 126 has a cross sectional area ($A_{LC}$) in a dimension parallel to electrodes 102 and 104 that is much smaller than a surface area ($A_{DB}$) of the dielectric barriers that face the gap, such as by at least one order of magnitude. In this example, the area $A_{LC}$ of aperture 126 is equal to $\pi r^2$, where "r" is the radius of aperture 126.

Figure 9:
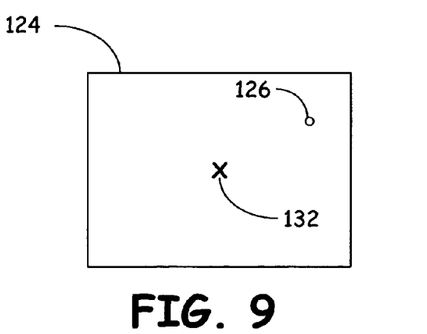
FIG. 9 is a top plan view of a separator having an aperture that is positioned remote from a geometric center of the separator, according to an alternative embodiment.

FIG. 9 illustrates a separator 124 having an aperture 126 that is positioned remote from a geometric center 132 of separator 124, according to an alternative embodiment.

Figure 10:
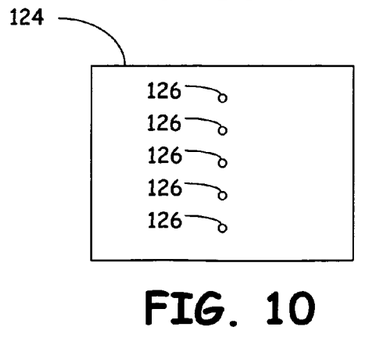
FIG. 10 is top plan view of a separator having a plurality of apertures arranged in a line.

FIG. 10 is top plan view of a separator 124 having a plurality of apertures 126 arranged in a line. Separator 124 can have any number of apertures 126 in any arrangement. The number, size and arrangement of apertures 126 simply affects the total area of the combined liquid channels through separator 124.

Figure 11:
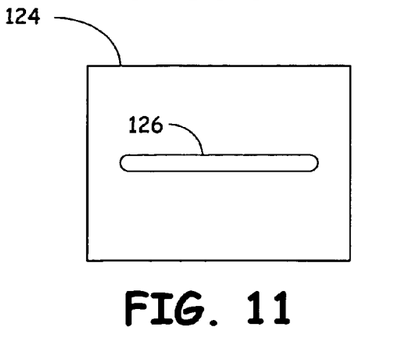
FIG. 11 is a top plan view of a separator having an oval aperture that forms a completely rounded rectangle according to a further embodiment.

FIG. 11 is a top plan view of a separator 124 having an oval aperture 126 that forms a completely rounded rectangle according to a further embodiment of the disclosure.

Figure 12:
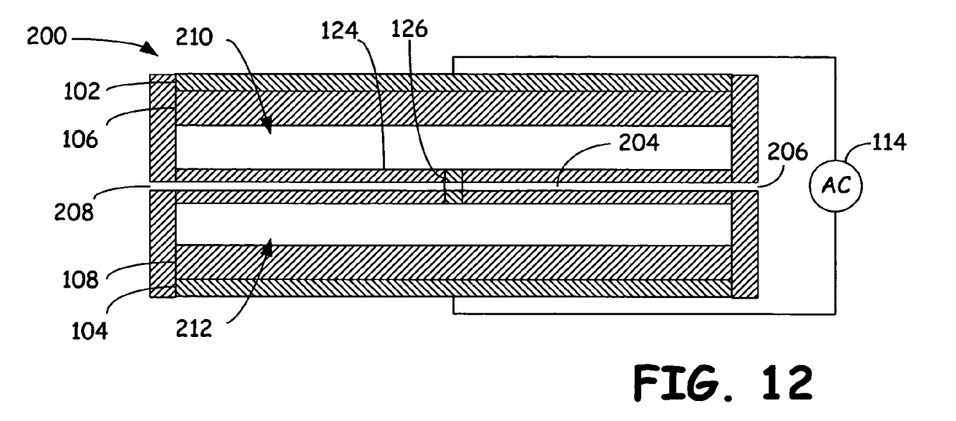
FIG. 12 is a cross-sectional view of a fluid treatment device having a conductive plug, according to a further alternative embodiment.

FIG. 12 is a cross-sectional view of a fluid treatment device 200 according to a further alternative embodiment. The same reference numerals are used in FIG. 12 as where used in the previous figures for the same or similar elements. Device 200 includes electrodes 102 and 104, dielectric barriers 106 and 108 and separator 124. As in the previous embodiments, separator 124 divides the gap between electrodes 102 and 104 into a first gap or chamber 210 and a second gap or chamber 212. However in this embodiment, the aperture 126 through separator 124 is filled with a conductive material 202 such as copper or a conductive polymer. Other conductive materials can also be used in alternative embodiments. Separator 124 further includes a lumen 204, which extends from inlet 206 to outlet 208 and passes through conductive material 202. Conductive material 202 forms a plug that physically isolates lumen 204 from chambers 210 and 212. In one embodiment, lumen 204 separates conductive material 202 into an upper portion and a lower portion, as shown in FIG. 12.

During operation, the liquid sample being treated is passed through lumen 204 from inlet 206 to outlet 208. The liquid sample in lumen 204 that resides in the area of aperture 126 completes an electrically conductive path from the top portion of conductive material 202 to the bottom portion of conductive material 202, thereby providing a conductive path from chamber 210 to chamber 212 while remaining physically isolated from chambers 210 and 212. The aperture therefore maintains an electric field passageway through dielectric separator 124, similar to the embodiments shown in FIGS. 3 and 7.

The portion of lumen 204 that passes through aperture 126 and plug 202 forms a small liquid treatment chamber in which the electric field lines of force are highly concentrated. This concentrating effect resulting from the small ratio of $A_{DB}$ to $A_{LC}$ significantly increases the efficacy of the liquid treatment in killing live pathogens living in the liquid or decomposing hazardous compounds contained in the liquid while permitting the device to be constructed with inexpensive materials and driven by an inexpensive power supply.

Since the liquid in lumen 204 is physically isolated from chambers 210 and 212, chambers 210 and 212 can be filled with a cooling liquid such as water, to provide for additional cooling during operation. The cooling liquid can be statically contained within the chambers or circulated through the chambers, for example.

In a further alternative embodiment, cooling chambers 210 and 212 are eliminated, with dielectric barriers 106 and 108 being positioned adjacent separator 124.

Figure 13:
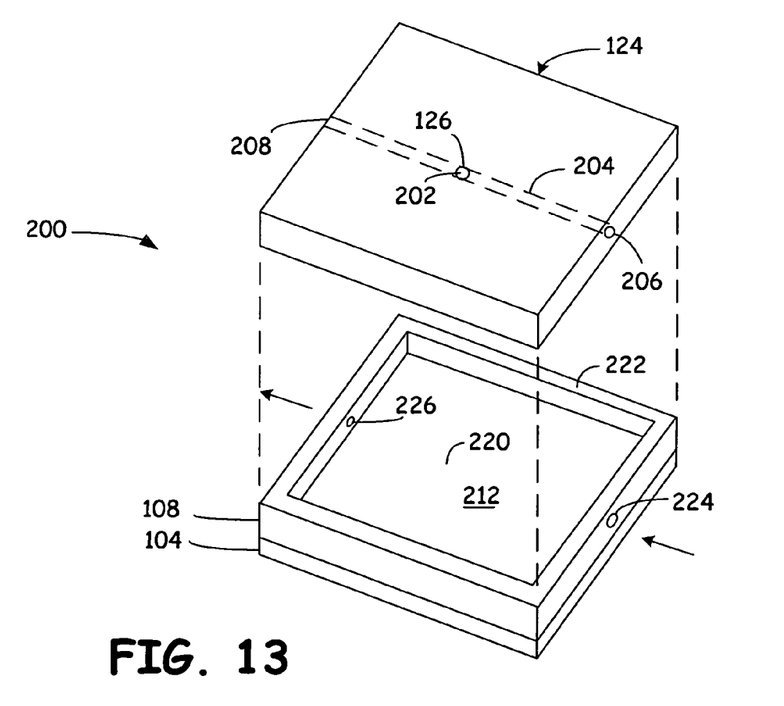
FIG. 13 is an exploded, perspective view of the bottom half of the device shown in FIG. 12.

FIG. 13 is an exploded, perspective view of the bottom half of device 200 according to one embodiment of the present invention. In this embodiment, electrode 104 includes a thin metallic sheet that is formed on the backside of dielectric barrier 108. Dielectric barrier 108 has a base 220 and side walls 222 that form the lower part of an enclosure for cooling liquid chamber 212. Dielectric barrier 108 further includes an inlet 224 and an outlet 226 through which cooling liquid can be passed into and out of cooling chamber 212. The upper electrode 102 and upper dielectric barrier 106 (shown in FIG. 12) can have a similar configuration as the lower electrode 104 and lower dielectric barrier 108 shown in FIG. 13.

As discussed with reference to FIG. 12, separator 124 includes an aperture 126 that is plugged with a conductive material 202. Lumen 204 extends through the material of separator 124 from inlet 206 to outlet 208. Lumen 204 passes through aperture 126 and the conductive material 202 contained therein. Lumen 204 can be routed through separator 124 in any pattern, and separator 124 can have any number of similar lumens and apertures. Each lumen 204 passes through at least one aperture 126. In one embodiment, lumen 204 has a serpentine path through separator 124, wherein each leg of the serpentine path has at least one aperture 126.

Figure 14:
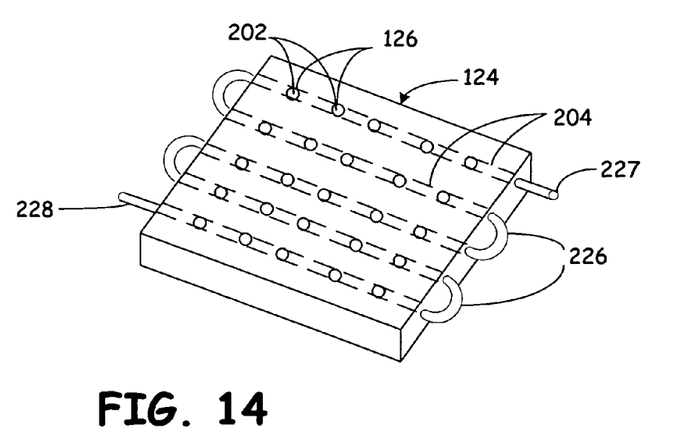
FIG. 14 is a perspective view of a separator according to a further alternative embodiment, which includes a plurality of pass-through lumens connected together by external tubing.

FIG. 14 is a perspective view of a separator 124 according to a further alternative embodiment. In this embodiment, separator 124 includes a plurality of pass-through lumens 204 extending from one side edge of the separator to an opposite side edge. Each lumen 204 passes through a plurality of apertures 126. Each aperture 126 is plugged with a conductive material 202. The ends of lumens 204 are connected through tubing 226 to define a serpentine treatment path extending from an inlet 227 to an outlet 228, wherein each leg of the path passes through a plurality of apertures 126. Therefore, as the liquid sample passes through the serpentine path, the sample becomes treated at numerous locations along the path, wherein each treatment further pasteurizes the sample.

Although separator 124 has a plurality of apertures 126, the ratio $A_{LC}/A_{DB}$ remains small to provide an electric field concentrating effect through the apertures. The number, size and arrangement of apertures 126 and lumens 204 can be selected to provide a desired concentration and/or treatment level, and the flow rate through the lumens can be set as desired.

In addition, multiple fluid treatment devices can be connected in series with one another to provide increased levels of treatment. Further, any of the devices disclosed herein can have a plurality of separators in any arrangement or spacing.

The liquid sample being treated and the cooling liquid can be passed through the respective chambers and lumens by any suitable method or device, such as with one or more pumps or by the operation of gravity. The liquid sample can also be passed through the same device multiple times.

Figure 15:
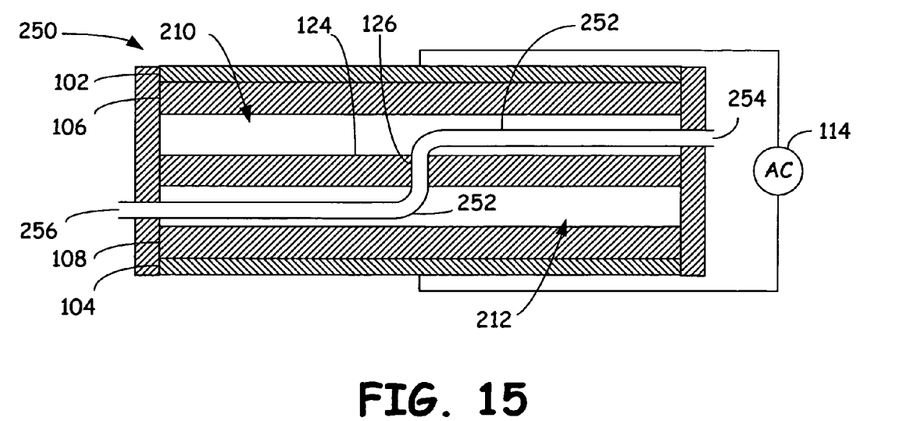
FIG. 15 is a schematic, cross-sectional view of a fluid treatment device in which the treatment flow path is isolated by tubing, according to a further alternative embodiment.

FIG. 15 is a schematic, cross-sectional view of a fluid treatment device 250 according to a further alternative embodiment. Again, the same reference numerals are used in FIG. 15 as were used in one or more of the 10 previous figures for the same or similar elements. Device 250 includes electrodes 102 and 104, dielectric barriers 106 and 108 and separator 124. As in the previous embodiments, separator 124 divides the gap between electrodes 102 and 104 into a first gap or chamber 210 and a second gap or chamber 212. However in this embodiment, the treatment fluid flow path is defined at least partially by at least one tube 252 extending from an inlet 254, through the first chamber 210 to aperture 126, and extending from aperture 126 through the second chamber 212 to outlet 256. Tubes 252 physically isolate the treatment fluid flow path from the first and second chambers 210 and 212. Thus, chambers 210 and 212 can contain a cooling liquid similar to the embodiment shown in FIGS. 12 and 13. This configuration also maintains the electric field passageway through aperture 126 through which the electric field lines of force are highly concentrated. As the liquid sample passes through the small treatment chamber formed by aperture 126, the liquid sample becomes exposed to a large, concentrated electric field.

One or more embodiments can be configured as desired either to avoid or to encourage the generation of highly reactive non-thermal plasma (NTP). Examples of modifications for encouraging the generation of NTP species are described in U.S. Pat. Nos. 6,562,386, 6,565,716, 6,911,225 and 7,011,790, which are hereby incorporated by reference. The devices shown and described above can be modified to include any of the features described in the reference patents. Conversely, the devices described in the referenced patents can be modified to include an electric field concentrator as described herein.

Figure 16:
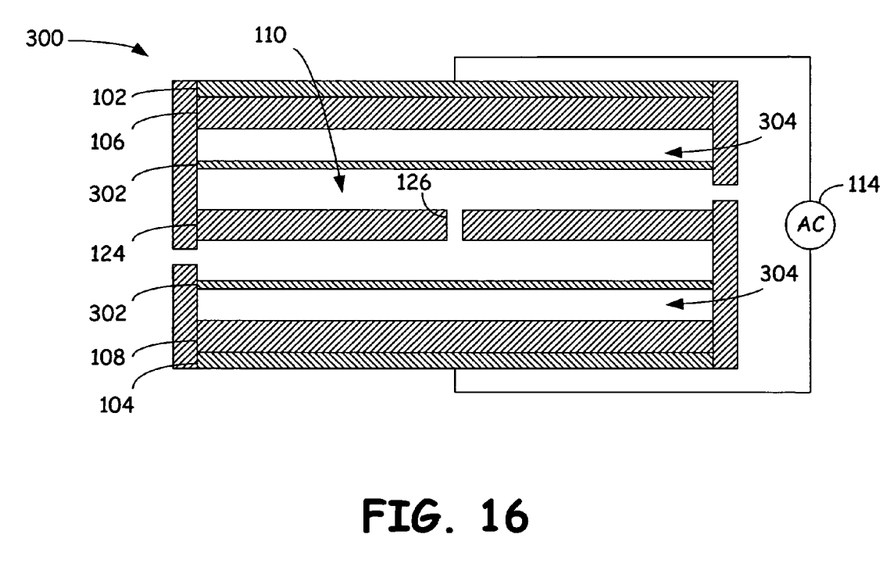
FIG. 16 is a schematic, cross-sectional view of a fluid treatment device having a discharge initiation region, according to a further alternative embodiment.

For example, device 100 shown in FIG. 3 can be modified to include a discharge initiation region, as shown in FIG. 16. The same reference numerals that were used in FIG. 3 are used in FIG. 16 for the same or similar elements. In this embodiment, device 300 includes films or plates 302, which divide the spaces between separator 124 and electrodes 102 and 104 into respective treatment chambers 110 and discharge initiation regions 304. Films 302 can be supported in the space between separator 124 and dielectric barriers 106 and 108 by peripheral spacers or sidewalls of the device, for example. Films 302 contain the liquid within treatment chambers 110 and prevent the liquid from entering discharge initiation regions 304. Discharge initiation regions 304 can be filled with various gases, such as air, another gas or a gas mixture. Discharge initiation regions 304 can also be substantially void of any gas and held under a vacuum at below-normal atmospheric pressure. In one embodiment, films 302 are formed of a dielectric material such as a transparent membrane of polytetrafluoroethylene from E. I. du Pont de Nemours and Company. In alternative embodiments, films 302 can be formed of a transparent epoxy resin or other types of film or sheet materials. Films 302 have good dielectric properties and allow one or more of the non-thermal plasma species to pass from discharge regions 304 to treatment chambers 110. Films 302 can also include non-dielectric material. Discharge initiation regions 304 and films 302 can have the structure and characteristics further described in U.S. Pat. No. 7,011,790, for example.

During operation, the resulting electric field between the electrodes generates non-thermal plasma species within discharge initiation regions 304. The non-thermal plasma species are easily generated and the discharge across regions 304 is fairly uniform. This assists in generating more consistent and uniform non-thermal plasma species within treatment chambers 110. The NTP species generated within initiation regions 304 that pass into the treatment chambers react with the liquid to kill more evenly and consistently pathogens living in the liquid.

Figure 17:
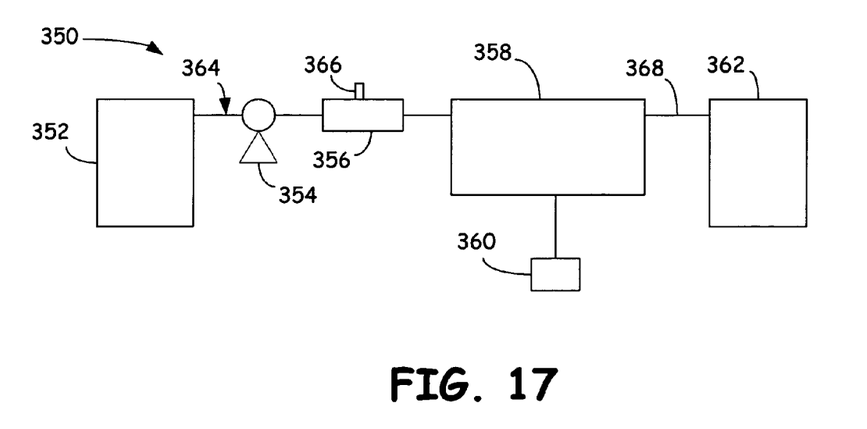
FIG. 17 is a block diagram illustrating a further alternative embodiment that introduces gas bubbles into the liquid being treated.

FIG. 17 is a block diagram illustrating a further alternative embodiment that introduces gas bubbles into the liquid being treated. System 350 includes liquid source tank 352, pump 354, gas mixing device 356, fluid treatment device 358, power supply 360 and liquid receiving tank 362. Source tank 352, pump 354, gas mixing device 356, fluid treatment device 358 and receiving tank 212 are coupled in series with one another along a treatment flow path 364, which can be formed of a series of tubes or other liquid channels for passing the liquid to be treated from one element in path 364 to the next.

Tank 352 contains the liquid to be treated. Pump 354 pumps liquid from tank 352 to tank 362, through treatment flow path 364. Additional pumps can be placed at various location along treatment flow path 364 in alternative embodiments. Also, pump 364 can be eliminated in embodiments in which another mechanism such as gravity, is used for moving the liquid along flow path 364. The output of pump 354 is coupled to the input of gas mixing device 206. The flow rate of the pump is set based on factors such as the desired treatment time, the applied voltage, the dimensions/structure of device 358, and the size of gas mixing device 354. Gas mixing device 354 can include any device that is capable of introducing gas bubbles into the liquid flowing through path 364. Various mixing devices can be used, such as a gas diffuser or gas injector. In one embodiment, gas mixing device 354 includes a Venturi tube injector. Gas mixing device 356 includes a gas inlet 366 for receiving the gas to be mixed into the liquid. The gas-liquid mixture is then provided to the inlet of device 358. In an alternative embodiment, gas mixing device 356 is eliminated.

Device 358 can include any of the devices shown and described herein, for example. Power supply 360 is electrically coupled to the electrodes within device 358. As the gas-liquid mixture passes through device 358, the non-thermal plasma an/or the electric field generated in device 358 disinfect the liquid by destroying at least a portion of the live pathogens such as bacteria or viruses living in the liquid. The treated liquid then exists device 358 and is collected in receiving tank 362.

With the embodiments described above an electric field concentrator concentrates the electric field within a small treatment portion of the reaction volume between the electrodes. The liquid sample being treated is passed along a treatment fluid path, which extends through the small treatment portion. By reducing the area of the treatment portion relative to the areas of the dielectric barriers and electrodes, the applied voltage and frequency need not be high. This allows the use of much lower cost power supplies while still achieving effective treatment levels. Also, by keeping the ratio of $A_{LC}$ to $A_{DB}$ small, the device does not require the use of very thin, very high dielectric constant materials for the dielectric barriers. Rather, less expensive material can be used that has a lower dielectric constant and a greater thickness. Also, a simple AC power supply can be used without requiring an expensive pulsed DC power supply. The structure can be configured to provide substantially less ohmic heating and does not require the electrodes to come in contact with the liquid. This significantly extends the useful life of the electrodes and further reduces cost. One or more of the structures disclosed above therefore overcomes many if not all of the drawbacks of a pulsed electric field (PEF) process while achieving the same or similar effectiveness.

Although the present invention has been described with reference to preferred embodiments, workers skilled in the art will recognize that changes may be made in form and detail without departing from the spirit and scope of the invention.

What is claimed is:

1. A fluid treatment device comprising:
    first and second electrodes, arranged to generate an electric field across a gap between the electrodes;
    a fluid treatment chamber located within the gap and electrically isolated from the first and second electrodes; and an electric field concentrator, which concentrates the electric field within the fluid treatment chamber, wherein the electric field concentrator comprises a dielectric separator, which divides the gap into a first gap between the first electrode and the separator and a second gap between the second electrode and the separator, and which comprises an electric field passageway extending through the separator from the first gap to the second gap.

2. The fluid treatment device of claim 1 and further comprising:
first and second dielectric barriers that electrically and physically isolate the first and second electrodes from the fluid treatment chamber.

3. The fluid treatment device of claim 1 and further comprising:
an inlet;
an outlet; and
a treatment fluid flow path, which extends from the inlet to the outlet and passes through the fluid treatment chamber.

4. The fluid treatment device of claim 1 and further comprising:
an inlet;
an outlet; and
a treatment fluid flow path, which extends from the inlet to the outlet and passes through the electric field passageway.

5. The fluid treatment device of claim 4 wherein the treatment fluid flow path passes from the first gap, through the electric field passageway to the second gap and is in fluid communication with the first and second gaps.

6. The fluid treatment device of claim 4 wherein the treatment fluid flow path is defined at least partially by at least one tube extending from the inlet, through the first gap to the electric field passageway, and extending from the electric field passageway through the second gap to the outlet, wherein the at least one tube physically isolates the treatment fluid flow path from the first and second gaps.

7. The fluid treatment device of claim 1 wherein the electric field concentrator further comprises:
an electrically conductive plug positioned within the electric field passageway;
a lumen, which defines a treatment fluid flow path and passes through the plug such that the plug physically isolates the lumen from the first and second gaps.

8. The fluid treatment device of claim 7 wherein the dielectric separator comprises a plurality of electric field passageways extending through the separator from the first gap to the second gap and each comprising a respective electrically conductive plug, wherein the lumen passes through the electrically conductive plugs of the plurality of electric field passageways.

9. The fluid treatment device of claim 7 wherein the first and second gaps are configured to contain cooling liquid.

10. The fluid treatment device of claim 9 wherein the first and second gaps each comprise a cooling liquid inlet and a cooling liquid outlet that define a cooling liquid flow path through the respective gap.

11. The fluid treatment device of claim 1 wherein the electric field passageway has a perimeter defined entirely by side walls that are formed by material of the dielectric separator such that the dielectric separator surrounds the passageway.

12. The fluid treatment device of claim 1 wherein the electric field passageway has a cross sectional area in a dimension parallel to the first and second electrodes that is smaller than a surface area of the electrodes that face the gap.

13. The fluid treatment device of claim 1 wherein the electric field passageway has a curvilinear perimeter.

14. The fluid treatment device of claim 1 wherein the perimeter has a shape selected from the group consisting of circular and oval.

15. The fluid treatment device of claim 1 wherein the electric field passageway is positioned generally at a geometric center of a cross section of the dielectric separator.

16. The fluid treatment device of claim 1 wherein the first and second electrodes are selected from the group consisting of parallel plate electrodes and coaxial electrodes.

17. A method comprising:
generating an electric field across a gap between first and second electrodes;
concentrating the electric field within the gap by dividing the gap into a first gap between the first electrode and a dielectric separator and a second gap between the second electrode and the dielectric separator, wherein the dielectric separator comprises an electric field passageway extending through the separator from the first gap to the second gap; and
passing a liquid through the electric field passageway during the step of generating the electric field.

18. The method of claim 17 wherein passing comprises:
passing the liquid through a lumen extending through a conductive plug that is positioned within the electric field passageway such that the plug physically isolates the liquid from the first and second gaps while allowing the electric field to pass through the liquid in the lumen.

* * * * *

UNITED STATES PATENT AND TRADEMARK OFFICE
CERTIFICATE OF CORRECTION

PATENT NO. : 7,931,811 B2
APPLICATION NO. : 11/588955
DATED : April 26, 2011
INVENTOR(S) : Rongsheng Ruan et al.

It is certified that error appears in the above-identified patent and that said Letters Patent is hereby corrected as shown below:

In the Specification

In Column 3: Equation 4, lines 44–48, delete

" $$U_L = IR_L = \frac{\pi f C_{DB}}{1 + \pi f C_{DB} R_L} U_o \times R_L$$ "

and insert therefor

-- $$U_L = IR_L = \frac{\pi f C_{DB}}{1 + \pi f C_{DB} R_L} U_a \times R_L$$ --.

Signed and Sealed this
Seventeenth Day of May, 2016

Michelle K. Lee
*Director of the United States Patent and Trademark Office*